US006077946A

United States Patent [19]
Iwanaga et al.

[11] Patent Number: 6,077,946
[45] Date of Patent: Jun. 20, 2000

[54] DNA ENCODING HORSESHOE CRAB AMEBOCYTE LYSATE FACTOR G SUBUNIT A

[75] Inventors: Sadaaki Iwanaga; Tatsushi Muta; Noriaki Seki, all of Fukuoka; Toshio Oda, Higashiyamato, all of Japan

[73] Assignee: Seikagaku Corporation, Japan

[21] Appl. No.: 09/330,945

[22] Filed: Jun. 11, 1999

Related U.S. Application Data

[62] Continuation of application No. 09/119,995, Jul. 21, 1998, abandoned, which is a division of application No. 08/392,828, filed as application No. PCT/JP94/01057, Jun. 29, 1994, Pat. No. 5,795,962.

[30] Foreign Application Priority Data

Jun. 29, 1993 [JP] Japan .................................. 5-184403

[51] Int. Cl.[7] ............................ C07H 21/02; C07H 21/04
[52] U.S. Cl. ......................................... 536/23.1; 536/25.1
[58] Field of Search ................................. 536/23.1, 23.5, 536/25.1; 435/320.1, 69.1

[56] References Cited

U.S. PATENT DOCUMENTS

| | | | |
|---|---|---|---|
| 4,107,077 | 8/1978 | Sullivan, et al. | 252/408 |
| 4,188,264 | 2/1980 | Iwanaga et al. | 23/230 B |
| 4,495,294 | 1/1985 | Nakahara et al. | 436/502 |
| 5,047,353 | 9/1991 | Tsuchiya et al. | 436/502 |
| 5,155,032 | 10/1992 | Tanaka et al. | 435/184 |
| 5,179,006 | 1/1993 | Matuura et al. | 435/23 |
| 5,316,911 | 5/1994 | Baek et al. | 435/7.9 |
| 5,318,893 | 6/1994 | Matuura et al. | 435/23 |
| 5,389,547 | 2/1995 | Tanaka et al. | 436/94 |

FOREIGN PATENT DOCUMENTS

| | | |
|---|---|---|
| 0 370 700 | 5/1990 | European Pat. Off. . |
| 0 500 947 | 9/1992 | European Pat. Off. . |
| 0 549 102 A1 | 6/1993 | European Pat. Off. . |
| 0569 033 A2 | 11/1993 | European Pat. Off. . |
| WO 92/15683 | 9/1992 | WIPO . |

OTHER PUBLICATIONS

Kang, A.S. et al.; "Antibody redesign by chain shuffling from random combinatorial immunoglobulin libraries" Proc. Natl. Acad. Sci. USA, vol. 88, Dec. 1991, pp. 11120–11123.

Qabar, A.N. et al.; "Hierarchy of globin complexes" Journal of Molecular Biology, vol. 222, 1991, pp. 1109–1129.

Muta, T. et al.; "Limulus factor C" Journal of Biological Chemistry, vol. 266, No. 10, Apr. 5, 1991, pp. 6554–6561.

Noriaki et al., "Horseshoe Crab (1,3)–β–D–Glucan–Sensitive Coagulation Factor G", *The Journal of Biological Chemistry*, 269, No. 2:1370–1374 (1994).

Sadaaki Iwanaga et al., "Role of Hemocyte–Derived Granular Components in Invertebrate Defense", *Annals of the New York Academy of Sciences*, 712:102–116 (1994).

*Primary Examiner*—W. Gary Jones
*Assistant Examiner*—Devesh Srivastava
*Attorney, Agent, or Firm*—Testa, Hurwitz & Thibeault, LLP

[57] ABSTRACT

This invention relates to a DNA shown by SEQ ID No. 1 and an amino acid sequence coded by said DNA. This invention also relates to a DNA and an amino acid sequence of subunit a of (1→3)-β-glucan sensitive factor derived from amebocytes of horseshoe crab and have potent affinity to (1→3)-β-D-glucan in cell walls of fungi. Therefore, the invention is useful for the diagnosis of fungal diseases and as antimicrobial or eradicating agent of fungi in combination with an antifungal agent.

4 Claims, 4 Drawing Sheets

```
FGA       4  PKWQLVWSDEFTNG--ISSDWEFEMGNGLN------GWGNNELQ   39
BG1 A1  421  AGMNLIWQDEFNGTTLDTSKWNYETGYYLNNDPATWGWGNAELQ  464

FGA      40  --YYRRENAQVEGGKLVITAKREDY------DGFKYTSARLKT   74
BG1 A1  465  HYTNSTQNVYVQDGKLNIKAMNDSKSFPQDPNRYAQYSSGKINT  508

FGA      75  QFDKSWKYGKIEAKMAIPSFRGVWVMEWMSGDNTHYVRWPSSGE  118
BG1 A1  509  KDKLSLKYGRVDFRAKLPTGDGVWPALWMLPKDSVYGTWAASGE  552

FGA     119  IDFIEHRNT------NNEKVRGTIHWSTPDGARAHHNRESHTNG  156
BG1 A1  553  IDVMEARGRLPGSVSGTIHFGGQWPVNQSSGGDYHFP-EGQTFA  595

FGA     157  IDYHIYSVEWNSSIVKWFVNGHQYFEVKIQ------GGVNGKSA  194
BG1 A1  596  NDYHVYSVVWEEDNIKWYVDGKFFYKVTNQQWYSTAAPNNPNAP  639

FGA     195  FRNKVFVILNMAIGGNWPGFDVADEAFPA-KMYIDYVRVYQDA   236
BG1 A1  640  FDEPFYLIMNLAVGGNFDGGRTPNASDIPATMQVDYVRVYKEQ   682
```

(PRIOR ART)

```
FGA    4  PKWQLVWSDEFTNG--ISSDWEFEMGNGLN------GWGNNELQ   39
BG1  421  AGMNLIWQDEFNGTTLDTSKWNYETGYYLNNDPATWGNAELQ       464

FGA   40  --YYRRENAQVEGGKLVHTAKREDY-------DGFKYTSARLKT       74
BG1  465  HYTNSTQNVYVQDGKLNHKAMNDSKSFPQDNRYAQYSSGKINT      508

FGA   75  QFDKSWKYGKIEAKMAIPSFRGVWMFWMSGDNTHYVRWPSSGE     118
BG1  509  KDKLSLKYGRVDFRAKLPTGDGVWPALWMLPKDSVYGTWAASGE    552

FGA  119  IDFIEHRNT------NNEKVRGTIHWSTPDGARAHHNRESHTNG    156
BG1  553  IDVMEARGRLPGSVSGTIHFGGQWPVNQSSGGDYHFP-EGQTFA    595

FGA  157  IDYHIYSVEWNSSIVKWFVNGHQYFEVKIQ------GGVNGKSA    194
BG1  596  NDYHVYSVWEEDNIKWYVDGKFFYKVTNQQWYSTAAPNNPNAP     639

FGA  195  FRNKVFVILNMAIGGNWPGFDVADEAFPA-KMYIDYVRVYQDA     236
BG1  640  FDEPFYLIMNLAVGGNFDGGRTPNASDIPATMQVDYVRVYKEQ     682
```

FIG. 2

```
FGA    SKLIQAESY--FDSSKVQLEDTSDVGGGKNVKCDNE   424
FGA    SKLIQAESY--ESYSEVQLEDTLDVGGGKNVKCDKE   562
Xyn  N NTRIEAEDYDGINSSIEIIGVPPEGGR-GIGYITS    332

FGA    GAWMAYKDIDFPSSGNYRIEYRVASERAGGKLSLDL   460
FGA    GAWMAYKDIDFPSSGSYRVEYRVASERAGGKLSLDL   598
Xyn  N GDYLVYKSIDEFGN-GATSFKAKVANAN-TSNIELRL   366

FGA    NAG-SIVLGMLDVPSTGGWQKWTTISHTVNVDSGTY    495
FGA    NAG-SIVLGMLDIPSTGGLQKWTTISHIVNVDLGTY    633
Xyn  N NGPNGTLIGTLSVKSTGDWNTYEEQTCSISKVTGIN   402

FGA    NLGIYVQRASWNINWIKIPEQSNLNQGRRN         528
FGA    NLGIYVQKASWNINWHRITKV                  654
Xyn  N DL-YLVFKGPVNIDWFTFGVESSSTGLGDLNGD      434
```

FIG. 3

```
FGA  R1  247  LDGYYFVQNRHSELYLDVTDASNEDGAFLQQWSYSGNENQQFDFEHL-  293
FGA  R2  294  ENNVYKITNKKSGKSLDVYNFGTENGVRIQQWSYGGARNQQFTVQSV-  340
FGA  R3  341  GDGYYKIIPRGSGKIVEVADFSKDAGGKIQQWSDNNQLSGQWKLIKS-  387 xln A R1  351  ADG-GQIKGVGSGRCLDVPDASTSDGTQLQLWDCHSGTNQQWAATDAG  397
xln A R2  398  ELRV-----GDKCLDAAGTS--NGSKVQIYSCWGGDNQKWRLNS---  435
xln A R3  436  -DG--SVVGVQSGLCLDAVGNGTANGTLIQLYTCSNGSNQRWTRT---  477
```

FIG. 4

DNA ENCODING HORSESHOE CRAB AMEBOCYTE LYSATE FACTOR G SUBUNIT A

This is a continuation of 09/119,995, filed Jul. 21, 1998, now abandoned, which is a divisional of 08/392,828, filed Feb. 28, 1995, now U.S. Pat. 5,795,962 which was nationalized in the United States based upon PCT/JP/01057.

FIELD OF THE INVENTION

This invention relates to a polypeptide derived from limulus (horseshoe crab) amebocytes shown by an amino acid sequence of (1→3)-β-D-glucan sensitive factor (hereinafter abbreviated as factor G) and a DNA encoding thereof, particularly to a polypeptide shown by an amino acid sequence of subunit a of factor G and a DNA encoding thereof.

BACKGROUND OF THE INVENTION

Heretofore, determination of endotoxin with a limulus amebocyte lysate has been known. This method is based on coagulation of lysate with a very small amount of endotoxin, for example at about $10^{-9}$ g. It has been elucidated with the progress of biochemistry that this coagulation reaction consists of the stepwise activation mechanism of some coagulation factors. (Takanori Nakamura et al., Jpn. J. Bacteriol., 38, 781–803 (1983)). FIG. 1 shows the coagulation cascade reaction of Japanese horseshoe crab (*Tachypleus tridentatus*). The structures of three serine protease precursors (factor C, factor B and proclotting enzyme) and a clottable protein (coagulogen) in FIG. 1 have been elucidated by studies such as cDNA cloning (i. Muta et al. (1991) J. Biol. Chem., 265, 22426–22433 and 266, 6554–6561, and T. Miyata et al (1986) J. Biochem., 100, 213–220).

The lysate has been known to react with (1→3)-β-D-glucan which exists in the cell walls of fungi and yeasts, at concentrations of $10^{-8}$–10–9 g to trigger coagulation (see FIG. 1). Factor G responds to (1→3)-β-D-glucans, initiating clot formation. It is reported that factor G is a serine protease precursor as well as the other factors and it is a glycoprotein composed of non-covalently associated subunits a (72 kDa) and b (37 kDa) (64th Annual Meeting of Japan Biochemical Society, 1991).

Additionally, subunit a of factor G has a specific binding site to (1→3)-β-D-glucan and subunit b has serine protease region. Factor G is supposed to be activated and express serine protease activity by the binding of (1→3)-β-D-glucan to subunit a. However, the complete structure of factor G remains unknown.

DISCLOSURE OF THE PRESENT INVENTION

The present invention was accomplished with these understandings and aims to isolate and purify the factor G derived from limulus amebocytes, particularly subunit a having a binding site with (1→3)-β-D-glucan and to elucidate its complete structure.

Another object of the present invention is to provide a polypeptide having a (1→3)-β-D-glucan binding site of a factor G and a DNA encoding thereof.

The other object of the present invention is to provide a polypeptide of subunit a of factor G and DNA encoding thereof.

Further object of the present invention is to provide a polypeptide of factor G containing subunit a and a DNA encoding thereof.

Therefore, the present invention relates to a single stranded DNA encoding for a polypeptide containing at least one motif structure shown by an amino acid sequence of (SEQ. ID No. 2) Gln-Gln-Trp-Ser, a double stranded DNA composed of said DNA and its complementary DNA, and a polypeptide shown by said amino acid sequence.

Furthermore, the present invention relates to a single stranded DNA encoding for a polypeptide consisted of below mentioned amino acid sequence or a homologous sequence thereof, a double stranded DNA composed of said DNA and its complementary DNA and a polypeptide shown by said amino acid sequence, (SEQ. ID No. 2):

Ser His Glu Pro Lys Trp Gln Leu Val Trp Ser Asp Glu Phe Thr

Asn Gly Ile Ser Ser Asp Trp Glu Phe Glu Met Gly Asn Gly Leu

Asn Gly Trp Gly Asn Asn Glu Leu Gln Tyr Tyr Arg Arg Glu Asn

Ala Gln Val Glu Gly Gly Lys Leu Val Ile Thr Ala Lys Arg Glu

Asp Tyr Asp Gly Phe Lys Tyr Thr Ser Ala Arg Leu Lys Thr Gln

Phe Asp Lys Ser Trp Lys Tyr Gly Lys Ile Glu Ala Lys Met Ala

Ile Pro Ser Phe Arg Gly Val Trp Val Met Phe Trp Met Ser Gly

Asp Asn Thr Asn Tyr Val Arg Trp Pro Ser Ser Gly Glu Ile Asp

Phe Ile Glu His Arg Asn Thr Asn Asn Glu Lys Val Arg Gly Thr

Ile His Trp Ser Thr Pro Asp Gly Ala His Ala His His Asn Arg

Glu Ser Asn Thr Asn Gly Ile Asp Tyr His Ile Tyr Ser Val Glu

Trp Asn Ser Ser Ile Val Lys Trp Phe Val Asn Gly Asn Gln Tyr

Phe Glu Val Lys Ile Gln Gly Gly Val Asn Gly Lys Ser Ala Phe

Arg Asn Lys Val Phe Val Ile Leu Asn Met Ala Ile Gly Gly Asn

Trp Pro Gly Phe Asp Val Ala Asp Glu Ala Phe Pro Ala Lys Met

-continued

```
Tyr Ile Asp Tyr Val Arg Val Tyr Gln Asp Ala Ser Thr Ser Ser

Pro Val Gly Asp Thr Ser Leu Asp Gly Tyr Tyr Phe Val Gln Asn

Arg His Ser Glu Leu Tyr Leu Asp Val Thr Asp Ala Ser Asn Glu

Asp Gly Ala Phe Leu Gln Gln Trp Ser Tyr Ser Gly Asn Glu Asn

Gln Gln Phe Asp Phe Glu His Leu Glu Asn Asn Val Tyr Lys Ile

Thr Asn Lys Lys Ser Gly Lys Ser Leu Asp Val Tyr Asn Phe Gly

Thr Glu Asn Gly Val Arg Ile Gln Gln Trp Ser Tyr Gly Gly Ala

Arg Asn Gln Gln Phe Thr Val Gln Ser Val Gly Asp Gly Tyr Tyr

Lys Ile Ile Pro Arg Gly Ser Gly Lys Leu Val Glu Val Ala Asp

Phe Ser Lys Asp Ala Gly Gly Lys Ile Gln Gln Trp Ser Asp Asn

Asn Gln Leu Ser Gly Gln Trp Lys Leu Ile Lys Ser Lys Ser Tyr

Ser Lys Leu Ile Gln Ala Glu Ser Tyr Phe Asp Ser Ser Lys Val

Gln Leu Glu Asp Thr Ser Asp Val Gly Gly Gly Lys Asn Val Lys

Cys Asp Asn Glu Gly Ala Trp Met Ala Tyr Lys Asp Ile Asp Phe

Pro Ser Ser Gly Asn Tyr Arg Ile Glu Tyr Arg Val Ala Ser Glu

Arg Ala Gly Gly Lys Leu Ser Leu Asp Leu Asn Ala Gly Ser Ile

Val Leu Gly Met Leu Asp Val Pro Ser Thr Gly Gly Trp Gln Lys

Trp Thr Thr Ile Ser His Thr Val Asn Val Asp Ser Gly Thr Tyr

Asn Leu Gly Ile Tyr Val Gln Arg Ala Ser Trp Asn Ile Asn Trp

Ile Lys Ile Thr Lys Ile Pro Glu Gln Ser Asn Leu Asn Gln Gly

Arg Arg Asn Ser Lys Leu Ile Gln Ala Glu Ser Tyr Phe Ser Tyr

Ser Glu Val Gln Leu Glu Asp Thr Leu Asp Val Gly Gly Gly Lys

Asn Val Lys Cys Asp Lys Glu Gly Ala Trp Met Ala Tyr Lys Asp

Ile Asp Phe Pro Ser Ser Gly Ser Tyr Arg Val Glu Tyr Arg Val

Ala Ser Glu Arg Ala Gly Gly Lys Leu Ser Leu Asp Leu Asn Ala

Gly Ser Ile Val Leu Gly Met Leu Asp Ile Pro Ser Thr Gly Gly

Leu Gln Lys Trp Thr Thr Ile Ser His Ile Val Asn Val Asp Leu

Gly Thr Tyr Asn Leu Gly Ile Tyr Val Gln Lys Ala Ser Trp Asn

Ile Asn Trp Ile Arg Ile Thr Lys Val
```

Four species of horseshoe crab have been known and the coagulogens which are components of amebocytes of these four species of horseshoe crab are very similar in their structure (73%–99%) that is necessary for the expression of their function. Thus, the polypeptides of the present invention derived from these four species of horseshoe crab are presumed to have similar amino acid sequence as well as that in coagulogen.

In other words, where there is a homology between polypeptides, there is an identical or similar functional expression with their similar amino acid sequences though they have no identical amino acid sequences. Therefore, person skilled in the art will easily understand that the present invention encompasses not only the above mentioned amino acid sequence but also its homologous amino acid sequences.

The present invention will be explained in detail.

Factor G can be isolated and purified from amebocyte lysate of horseshoe crab by various column chromatography techniques, for example, affinity chromatography with dextran sulfate-Sepharose$^{RTM}$ CL-6B and Concanavalin A-Sepharose$^{RTM}$ 4B, gel filtration chromatography such as Sephacryl$^{RTM}$ S-200HR (T. Morita et al. (1981) FEBS Lett., 129(2), 318–321, Japanese Published Examined Patent Application (herein after abbreviated as Japan Tokkyo Koho) No. 399 (1991). Furthermore, subunits a and b which constitute factor G can be obtained by denaturation of factor G with a denaturing agent such as a surfactant followed by fractionation with high performance liquid chromatography (hereinafter abbreviated as HPLC) using a molecular sieve. The partial amino acid sequences of the each subunits can be determined by the following; each subunit is subjected to reduction and alkylation and enzymic digestion to give peptide fragments, and the amino acid sequence of the peptide fragments is determined by a peptide sequencer and so on. cDNAs encoding for the each subunits are isolated from the cDNA libraries, which are prepared from poly(A)+ RNA isolated from limulus amebocytes, using antibodies to each subunits or oligonucleotides synthesized according to aforementioned partial amino acid sequences of each subunits. Then the nucleotide sequence of these cDNA can be determined using dideoxy chain termination method (Sanger, F. et al., Proc. Natl. Acad. Sci. U.S.A., 74, 5463–5467 (1977)). The amino acid sequences of each subunits can be determined from above mentioned nucleotide sequences and partial amino acid sequences.

cDNA (AGC . . . . GTG; base Nos. 114–2,075) encoding for polypeptide of subunit a of factor G shown in sequence No. 1 and the corresponding amino acid sequence (Ser . . . . Val; amino acid Nos. 1–654) are determined according to the above mentioned method.

Further, subunit a of factor G was found to have a domain structure from its amino acid sequence.

That is, a glucanase domain having amino acid- sequence similar to that of carboxyl terminal of β-1,3-glucanase was found in the amino terminal of subunit a (Pro . . . Ala; amino acid Nos. 4–236) (FIG. 2). While, the carboxyl terminal portion of subunit a has a repetitive structure composed of 126 amino acids (Ser . . . . Ile; amino acid Nos.-391–516 and Ser . . . . Val; amino acid Nos. 529–654), and this sequence is similar to that of amino terminal portion of xylanase Z (FIG. 3). Furthermore, a "QQWS (Gln-Gln-Trp-Ser)(SEQ. ID No. 34)" motif is contained between domains of glucanase and xylanase, and three repetitions of a sequence similar to that-of xylanase A (Leu . . . . Leu; amino acid Nos. 247–293, Glu . . . . Val; amino acid Nos. 294–340 and Gly . . . . Ser; amino acid Nos. 341–387) (FIG. 4).

Additionally, FIG. 2–4 showed each amino acid with one letter code.

In the present invention, recombinant DNA vectors including the DNA encoding for these peptides are prepared and transfected into hosts and cultured or bred with so-called gene technology to produce and collect desired peptides.

BRIEF EXPLANATION OF THE DRAWINGS

FIG. 2 shows the amino acid sequence of glucanase domain of subunit a (amino acid Nos. 4–236). In the Fig., FGA indicates an amino acid sequence of amino acid Nos. 4–236 of subunit a of factor G, and β G1 A1 indicates an amino acid sequence of amino acid Nos. 421–682 of β-1, 3-glucanase.

FIG. 3 shows a domain of amino acid Nos. 391–654 in subunit a of factor G. In the Fig., FGA indicates an amino acid sequence of amino acid Nos. 391–654 of subunit a of factor G, and Xyn Z indicates an amino acid sequence of amino acid Nos. 298–434 of xylanase Z.

FIG. 4 shows a domain of amino acid Nos. 247–387 of subunit a of factor G. In the Fig., FGA indicates an amino a acid sequence of amino acid Nos. 247–387 of subunit a of factor G, and Xln A indicates an amino acid sequence of amino acid Nos. 351–477 of xylanase A.

THE BEST MODE TO PERFORM THE INVENTION

Figure 1:
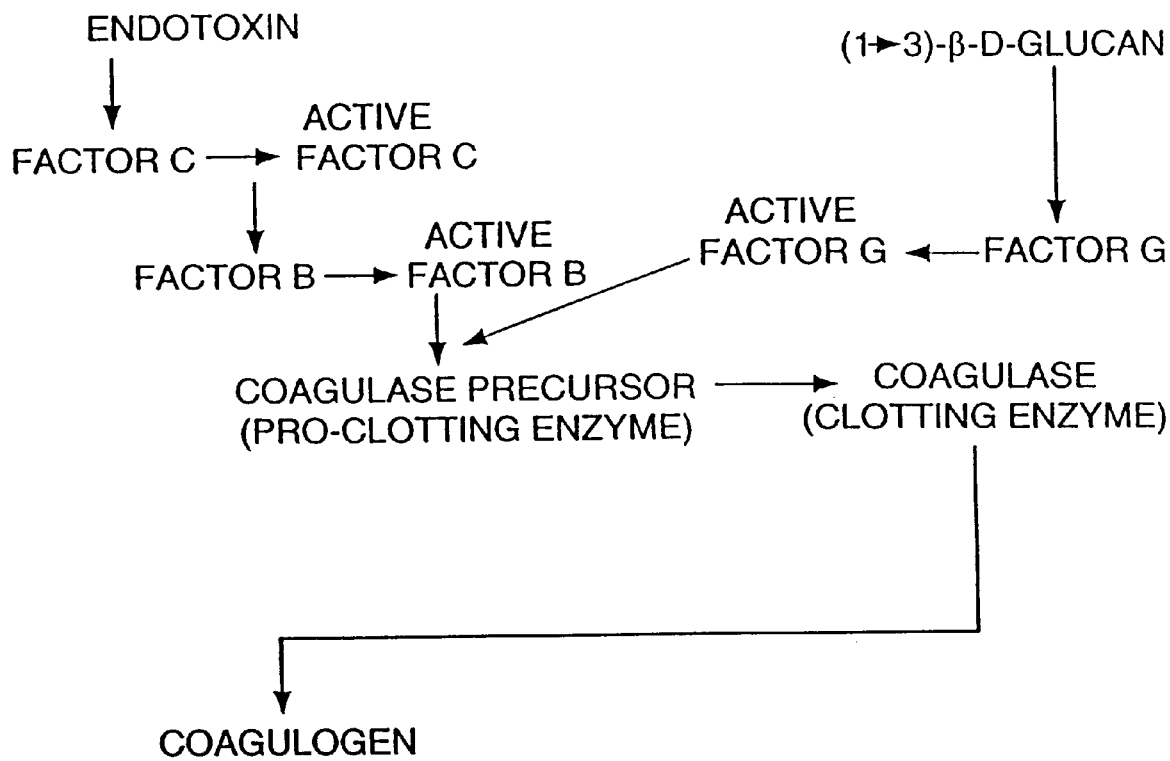
FIG. 1 shows the mechanisms of endotoxin sensitive and (1→3)-β-D-glucan sensitive coagulation cascade reaction of horseshoe crab amebocyte.
Figure 1:
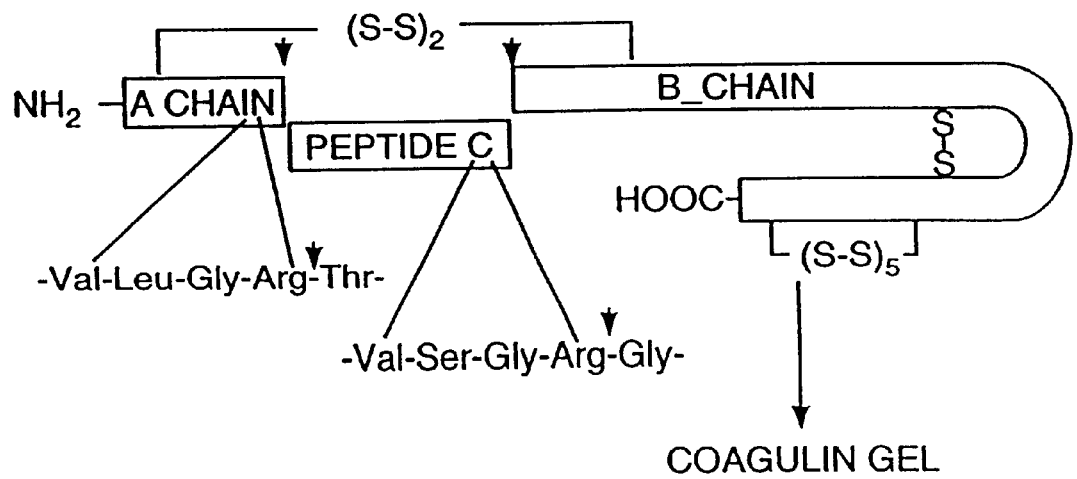

The present invention will be explained by the following practical examples, however, the scope of the invention is not restricted by these examples.

EXAMPLE 1

1. Purification of Factor G (1) Preparation of amebocyte lysate 400 ml of 0.02M Tris-HCl buffer containing 50mM NaCl, pH 8.0 was added to 113 g of amebocytes of Tachypleus tridentatus, and homogenized for three minutes with a high speed homogenizer (Hyscotron$^{RTM}$, Nippon Seimitsu Kogyo Co., Ltd.) and then centrifuged at 8,000 rpm for 30 min. to obtain a supernatant. Further, 300 ml of the same buffer was added to the resultant precipitates, homogenized and centrifuged in a similar manners to obtain a supernatant. The similar procedure was repeated further twice. All supernatants obtained by centrifugation were combined and 1,250 ml of amebocyte lysate was obtained.

(2) Purification of factor G from the amebocyte lysate.

a. Dextran sulfate-Sepharose CL-6B column chromatography.

The obtained 1,250 ml of extract was applied to a dextran sulfate-Sepharose$^{RTM}$ CL-6B column (5×17.8 cm) equilibrated in advance with the extraction buffer. The preparation of the column is performed according to the method shown in Japan Tokkyo koho No. 399 (1991) preparative example 2. The applied column was washed thoroughly with the same buffer and washed with 0.02M Tris-HCl buffer containing 0.15M NaCl, pH 8.0, to wash out the excess amount of protein which adsorbed into the column. The adsorbed protein into the column was eluted with 0.02M Tris-HCl buffer containing 0.25M NaCl, pH 8.0, to obtain factor G fraction.

b. Concanavalin A-Sepharose$^{RTM}$ 4B column chromatography.

The above mentioned factor G fraction was applied to a Con A-Sepharose$^{RTM}$ 4B column (Pharmacia Biotech K.K.) (2×16 cm) equilibrated with 0.02M Tris-HCl buffer containing 0.25M NaCl, pH 8.0, washed thoroughly with the equilibration buffer and 0.02M Tris-HCl buffer containing 0.5M NaCl, pH 8.0, successively, then, the protein which adsorbed into the column was eluted with 0.02M Tris-HCl buffer containing 0.5M each of NaCl and methyl α-D-glucoside, pH 8.0, to obtain factor G fraction.

c. Sephacryl S-200 HR column chromatography The above mentioned factor G fraction was concentrated with ultrafiltration and applied to a Sephacryl$^{RTM}$ S-200 HR column (Pharmacia Biotech K.K.) (2.7×98 cm) equilibrated with 0.05M sodium phosphate buffer, pH 6.5, and protein was eluted with the same buffer. The final eluate fraction of this chromatography containing the protein with slight absorbance at 280 nm was collected to obtain the protein of finally purified preparation of factor G. About 300 μg of factor G calculated as bovine serum albumin was obtained from 113 g of amebocytes.

2. Determination of Partial Sequence of Subunit a of Factor G (1) Separation of subunits a and b of factor G Subunits a and b of factor G were separated for the elucidation of partial amino acid sequences of subunits a and b required for cDNA cloning of subunits a and b of factor G. The factor G obtained in the above mentioned 1 was precipitated with methanol and chloroform for desalting and concentration (Methods in Enzymology, 182, p. 78–79 (1990)). The resultant precipitates were dissolved in 2% sodium dodecylsulfate (SDS) solution, and heated at 100° C. for 5 min. This heated sample was applied to gel filtration by using a tandem columns of TSKgel$^{RTM}$ G3000SW (TOSOH Corp.) using 0.1M sodium phosphate buffer containing 0.1% SDS, pH 7.0, as a mobile phase, and subunits a and b of factor G were separated.

(2) Enzymic digestion of subunit a of factor G Trichloroacetic acid (TCA) was added to give final concentration of 17.4 w/v % into the fraction of subunit a of factor G which obtained by above mentioned 2(1), and subunit a of factor G was precipitated. According to the method of Paul Matsudaira (A Practical Guide to Protein and Peptide Purification for Microsequencing, p. 42–43, 1989, Academic Press, Inc.), the precipitated subunit a of factor G was dissolved in 0.4M ammonium bicarbonate containing 8M urea and caused to reduction and alkylation with iodoacetamide. The reaction mixture was added with water to give 4M urea concentration, and lysyl endopeptidase (Wako Pure Chemical Ind. Ltd.) was added at an enzyme-substrate weight ratio of 1:60 and digestion was performed at 37° C. for 20 hrs. The digested product was applied to a α Bondasphere$^{RTM}$ 5 μ C8-300 angstrom (Waters Co., Ltd.) column (2.1×150 mm) preliminarily equilibrated with 0.06 v/v % trifluoroacetic acid and the column was thoroughly washed and eluted with acetonitrile using a linear concentration gradient method of 0 v/v % at 5 min., 24 v/v % at 65 min., 56 v/v % at 125 min. and 80 v/v % at 135 min. at a flow rate of 0.2 ml/min. to elute the adsorbed protein. The eluted peptides were monitored with UV absorbance at 210 nm, and completely collected.

(3) Determination of partial amino acid sequence.

The amino acid sequence of obtained each peptide was determined with a gas phase sequencer Model 477A (Applied Biosystems Japan Inc.). The results are shown in Table 1.

TABLE 1

Peptide 1 (SEQ. ID NO. 5)
Ser-Xaa-Glu-Pro-Lys-Xaa-Gln-Leu-Val-

Peptide 2 (SEQ. ID NO. 6)
Arg-Glu-Asp-Tyr-Asp-Gly-Phe-Lys

Peptide 3 (SEQ. ID NO. 7)
Tyr-Thr-Ser-Ala-Arg-Leu-Lys

Peptide 4 (SEQ. ID NO. 8)
Thr-Gln-Phe-Asp-Lys

Peptide 5
Ser-Trp-Lys

Peptide 6
Tyr-Gly-Lys

TABLE 1-continued

Peptide 7 (SEQ. ID NO. 9)
Met-Ala-Ile-Pro-Ser-Phe-Arg-Gly-Val-Trp-Val-Met-Phe-Trp-Met-Ser-Gly-Xaa-Asn-Thr-Asn-Tyr-Val-Xaa-Xaa-Pro- Peptide 8 (SEQ. ID NO. 10)
Ser-Ala-Phe-Arg-Asn-Lys Peptide 9 (SEQ. ID NO. 11)
Val-Phe-Val-Ile-Leu-Asn-Met-Ala-Ile-Gly-Gly-Asn-Xaa-Pro-Gly-Phe-Xaa-Val-Ala- Peptide 10 (SEQ. ID NO. 12)
Ile-Ile-Pro-Arg-Gly-Ser-Gly-Lys Peptide 11 (SEQ. ID NO. 13)
Val-Gln-Leu-Glu-Asp-Thr-Ser-Asp-Val-Gly-Gly-Gly-Lys Peptide 12 (SEQ. ID NO. 14)
Cys-Asp-Asn-Glu-Gly-Ala-Trp-Met-Ala-Tyr-Lys Peptide 13 (SEQ. ID NO. 15)
Asp-Ile-Asp-Phe-Pro-Ser-Ser-Gly-Asn-Tyr-Xaa-Ile-Glu-Tyr-Xaa-Val-Ala- Peptide 14 (SEQ. ID NO. 16)
Leu-Ile-Gln-Ala-Glu-Xaa-Tyr-Phe-Xaa-Tyr-Xaa-Glu-Val-Gln-Leu-Glu- Peptide 15 (SEQ. ID NO. 17)
Glu-Gly-Ala-Trp-Met-Ala-Tyr-Lys Peptide 16 (SEQ. ID NO. 18)
Val-Arg-Gly-Thr-Ile-His-Trp-Ser-Thr-Pro-Asp-Gly-Ala-His-Ala-His-His-Asn-Arg- In the formula, Xaa represents one of naturally occurring amino acids.

3. Synthesis of Oligonucleotide

In the determined amino acid sequences shown in Table 1, two amino acid sequences A (SEQ. ID. No. 6): -Glu-Asp-Tyr-Asp-Gly-Phe- and B(SEQ. ID No. 9): -Trp-Val-Met-Phe-Trp-Met- were selected and reverse translated as a sense in the case of A and as an antisense in the case of B. A mixture of 25 mer and 26 mer oligonucleotides shown below having recognition sequence of restriction enzyme and two bases for protection of DNA at 5'-terminal were synthesized with a DNA synthesizer 380A (Applied Biosystems Japan Inc.).

[FORMULA 1]

A': 5'-CGGAGCTCGAAGATTATGATGGTTT-3'  25 mer (SEQ. ID NO. 19)

G C C C C

A

G

-continued

[FORMULA 1]

```
B':  3'-ACCCATTACAAAACCTACCTTAAGGC-5'  26 mer (SEQ. ID NO. 20)
            C G
            A
            G
```

The oligonucleotides A' and B' shown above include all possibilities of sequences corresponding to A and B or complementary sequences thereof (however, the third nucleotide (T, C) in codon of Phe in A (TT(C/T)) was excluded).

4. Preparation of Poly(A)⁺RNA containing mRNA encoding for Factor G

Since poly(A)⁺ RNA was isolated from amebocytes of horseshoe crab, factor G is purified from amebocytes of horseshoe crab.

(1) Preparation of total RNA

By using of AGPC method (Experimental Medicine (Jikken Igaku) 9, 1937–1940 (1991), Pub. by Yodosha Co., Ltd.), about 11 mg of total RNA was isolated from 11.8 g of limulus amebocytes.

(2) Preparation of poly(A)⁺ RNA

Poly(A)⁺ RNA was isolated from about 2 mg of the above mentioned total RNA with Oligotex-dT$^{RTM}$ 30 Super kit (Nippon Roche K.K.). The similar procedure was repeated once again for further purification to obtain 34.5 µg of highly purified poly(A)⁺ RNA from 2 mg of total RNA.

5. Preparation of cDNA Library of Amebocytes of Horseshoe Crab (1) Synthesis of cDNA cDNA was synthesized from 5 µg in 34.5 µg of poly(A)⁺ RNA obtained in the above mentioned 4 with a cDNA synthesis kit (Amersham Co. Ltd.).

(2) Preparation of cDNA library cDNA library of amebocytes of horseshoe crab was prepared from cDNA synthesized in the above mentioned (1) by a cDNA cloning system λ gt10 adapter method (Amersham Co. Ltd.).

6. cDNA Cloning of Subunit a of Factor G cDNA fragment encoding for a part of subunit a of factor G was amplified with the oligonucleotide prepared in the above mentioned 3 using poly(A)⁺ RNA prepared in the above mentioned 4 (2) as a template by PCR method (Saiki, R. K., et al. Science, 239, 487–491, (1988)). The amplified cDNA fragment was labeled with [α-$^{32}$P]dCTP using Multiprime-DNA labeling kit (Nippon Gene Co., Ltd.) to obtain a probe. The probe was used for the screening of cDNA library prepared in above mentioned 5 (2) to obtain two positive clones containing a longest insert cDNA having about 2,400 bp. The insert cDNA of these clones were almost identical except for the length difference of 5'- and 3'-terminals in several bases, and their nucleotide sequences were determined. The composite nucleotide sequence contained an initiation codon and poly(A)⁺ tail, and showed the length of 2,408 bp.

7. Determination of Nucleotide Sequence of cDNA encoding for Subunit a of Factor G The insert cDNA prepared in the above mentioned 6 was integrated in pUC118 vector and pBluescriptII SK vector. The determination of total nucleotide sequences of cDNA cloned in pUC118 vector and pBluescriptllSK vector was performed by subcloning with deletion using restriction enzyme recognition site on cDNA fragment and kilosequence deletion kit (Takara Shuzo Co., Ltd.). The nucleotide sequence of cDNA in the clone prepared by the above mentioned procedure was determined with a DNA sequencer 370A (Applied Biosystems Japan Inc.) using fluorolabeled nucleotide primer (Smith, L.M. et al. (1986), Nature 321, 674–679).

The determined nucleotide sequence of cDNA of subunit a of factor G, and the deduced amino acid sequence were shown in SQ ID No. 1 of the Sequence listing. The partial amino acid sequences determined in 2 (3) (Table 1) are all included in the above mentioned amino acid sequence, and the inserted cDNA whose nucleotide sequence was determined by the procedure, was confirmed its encoding of subunit a of factor G.

8. Expression and Purification of Factor G or Subunits thereof

Whole or partial gene encoding for subunit a of factor G was cut out from the clone obtained above with ultrasonic wave or restriction enzyme treatment, or the other methods known in the art and integrated to a suitable vector. Vectors which constructed from such as phages or plasmids which autonomously proliferate in host microorganisms or cells for gene recombination including suitable promoters, SD sequences, translation initiating codon ATG, and suitable structural gene can be preferably used. These constructed vectors are integrated to obtain transformants in a suitable host organisms or cells, such as various strains of *E. coli* and yeasts, animal cells (e.g. oocytes of mice -and rats, Chinese hamster oocytes (CHO)), plant cells and insect cells or animal, plant or Insect hosts. The resultant transformant is cultured in a nutrient medium or bred with nutrient feeds to have stable production of large amount of factor G or subunit thereof (hereinafter abbreviated as factor G etc.). Culture or breeding conditions of the transformant may be suitably modified within the scope of factor G etc. production and conventional conditions known well to persons skilled in the art for the growth of hosts can be preferably used. Factor G etc. in the cultured products or bred animals can be collected from extracts of mechanically ground cultured solution containing microorganisms or cells, or individuals. However, when factor G etc. exist in the cultured solutions or extracts, factor G etc. are generally used after separating solutions containing factor G etc. from microorganisms, cells or ground individuals by filtration or centrifugation. When factor G etc. exist in microorganisms, cells, or organ membranes of individuals, microorganisms, cells or particles are collected by the filtration or centrifugation of the obtained cultured products or particles, and solubliized by mechanical or ultrasonic treatment, enzymic treatment with lysozyme and so on, addition of a chelating agent such as EDTA and/or a surfactant to separate and collect the factor G etc. The solutions containing factor G etc. obtained above can be isolated by conventional protein purification methods.

Factor G etc. expressed as a chimera polypeptide can be easily isolated by application of the properties of the other proteins. For example, the aimed factor G etc. can be easily isolated with affinity chromatography by-applying the affinity of the other proteins.

Practically, subunit a of factor G can be expressed by the following procedure.

An oligonucleotide having a sequence of (SEQ. ID No. 21) 5'-AGCCACGAACCAAAGTGGCA-3' is synthesized and its 5'-terminal is phosphorylated. The resultant oligonucleotide is annealed with a single-stranded DNA prepared from a plasmid integrated with a gene encoding for the subunit a of factor G, and elongation reaction was performed with DNA polymerase such as Klenow fragment. The single-stranded portion produced in this procedure is digested with a DNA nuclease such as Mung bean nuclease to obtain a double-stranded DNA. The resultant double-stranded DNA is digested with Sph I restriction enzyme and the produced cohesive ends are blunted with T4 DNA polymerase, Klenow fragment or Blunting kit. This double-stranded DNA is preliminarily digested with Nco I restriction enzyme and then the resultant cohesive end is integrated to pTV118N contained ampicillin resistant gene which was blunted with T4 DNA polymerase, Klenow fragment or a Blunting kit. The produced plasmid is transfected into *E. coli* JM109 or *E. coli* MY1184 to obtain transformant. The aimed transformant can be selected by applying conventional methods using the properties of plasmid. That is, a transformed microorganism is cultured on a LB plate contained ampicillin which is preliminarily sprayed with 5-bromo-4-chloro-3-(3-indolyl)-,β-D-galactoside (X-gal)/isopropylthiogalactoside (IPTG) and white colonies which transducted with the aimed plasmid are picked up and selected. Further screening with a synthetic oligonucleotide probe of (SEQ. ID No. 22) 5'-AAACAGACCATGAGCCACGAACCA-3' gave the plasmid with correct sequence. Furthermore, it can be confirmed by DNA sequencing with a sequencing primer using RV-N primer (Takara Shuzo Co., Ltd.) whether the plasmid was constructed correctly. *E coli* JM109 or *E coli* MV1184 transfected with the plasmid with correct sequence is cultured in a 3%. Nutrient broth (Nissui Pharmaceutical Co., Ltd.) containing 100 μg/ml ampicillin and 1 mM IPTG at 30° C. for 24 hrs. Subunit a of factor G is purified the cultured supernatant or extract of microorganisms by conventional methods. An affinity chromatography with antibody or a ligand having affinity to subunit a of factor G is preferably used for the more simple purification.

EXAMPLE 2

1. Determination of Partial Amino Acid Sequence of Subunit b of Factor G (1) Isolation of subunit b of factor G Subunit b can be similarly isolated according to Example 1, 2. (1) by separation of subunits a and b.

(2) Enzymic digestion of subunit b of factor G

Peptide fragments were obtained by the same method as Example 1, 2. (2) from subunit b of factor G obtained by above mentioned (1).

(3) Determination of partial amino acid sequence

The respective amino acid sequence of obtained peptides were determined by a similar manner to that of Example 1, 2. (3). The results are shown in Table 2.

TABLE 2

Peptide 1 (SEQ. ID NO. 23)
Gly-Ile-Asn-Glu-Lys

Peptide 2 (SEQ. ID NO. 24)
Xaa-Xaa-Gly-Phe-Xaa-Pro-Val-Ile-Thr-

Peptide 3 (SEQ. ID NO. 25)
Ile-Ile-Gly-Gly-Gly-Ile-Ala-Thr-Pro-His-Ser-Xaa-Pro-Xaa-Met-Val-Gly-Ile-Phe- Peptide 4
Val-Asn-Pro- Peptide 5 (SEQ. ID NO. 26)
Val-Xaa-Val-Val-Thr-Ala-Ala-His-Cys-Leu-Val-Thr-Gln-Phe-Gly-Asn-Arg-Gln-Xaa-Tyr-Ser-Ile-Phe-Val-Arg-Val-Gly-Ala-His-Xaa-Ile-Xaa-Asn-Ser-Gly-Thr-Asn- Peptide 6 (SEQ. ID NO. 27)
Val-Val-Ile-Thr-Gly-Trp-Gly-Val-Thr-Gly-Lys Peptide 7 (SEQ. ID NO. 28)
Asn-Val-Leu-Arg-Glu-Leu-Glu-Leu-Pro-Val-Val-Thr-Asn-Glu-Gln-Cys-Xaa-Lys Peptide 8 (SEQ. ID NO. 29)
Ser-Tyr-Gln-Thr-Leu-Pro-Phe-Ser-Lys Peptide 9 (SEQ. ID NO. 30)
Leu-Asn-Arg-Gly-Ile-Thr-Asn-Asp-Met-Ile-Cys-Ala-Gly-Phe-Pro-Glu-Gly-Gly-Lys Peptide 10 (SEQ. ID NO. 31)
Asp-Ala-Cys-Gln-Gly-Asp-Ser-Gly-Gly-Pro-Leu-Met-Tyr-Gln-Asn-Pro-Thr-Thr-Gly-Arg-Val-Lys 2. Synthesis of Oligonucleotide In the determined amino acid sequences, two amino acid sequences C: -Asn-Glu-Gln-Cys-(Asn)-Lys and D: -Met-Tyr-Gln-Asn-Pro-Thr- were used for reverse translation of C and D as sense and antisense, respectively, and the mixture of oligonucleotides C' and D' each having 25 nucleotides as shown below were synthesized in a similar manner to that of Example 1, 3.. In the C, -(Asn)- means presumed as Asn.

FORMULA 2

C': 5'-CGGAGCTCAATGAACAATGTAATAA-3'  25 mer (SEQ. ID NO. 32)

C G G C C

D': 3'-TACATAGTTTTAGGTTGCTTAAGGC-5'  25 mer (SEQ. ID NO. 33)

-continued
FORMULA 2

G C G C

A

G

The oligonucleotides C' and D' shown above include possibility of all the sequences corresponding to C and D, or complementary sequences. However, the C-terminal amino acid Lys of C and D, and Thr in D exclude the third nucleotides (A and G, and T, C, A, and G, respectively) in the respective codon of AA(A/G) and AC(A/C/G/T).

4. cDNA Cloning of Subunit b of Factor G

Using the poly(A)$^+$ RNA obtained by Example 1, 4. (2) as a template and the oligonucleotide synthesized by the above mentioned 2, the experiment was performed in a similar manner to that of Example 1, 6., and a positive clone having 1,979 bp of cDNA was obtained. The nucleotide sequence of insertion cDNA in the clone was analyzed and included a nucleotide sequence corresponding to amino acid sequence of peptide derived from subunit b of factor G obtained by the above mentioned 1. (2), and poly A additional signal. The clone was presumed to have full length of cDNA from its size.

5. Determination of cDNA Nucleotide Sequence Encoding for Subunit b of Factor G The nucleotide sequence of CDNA of subunit b of factor G was determined by a similar manner to that of Example 1, 7. The determined nucleotide sequence of cDNA of subunit b of factor G and amino acid sequence determined from the nucleotide sequence is shown in sequence No. 2 in the Sequence Listing.

The amino acid sequence includes all of partial amino acid sequences determined by Example 2, 1 (3) and shown in Table 2, thus, the determined nucleotide sequence of insertion CDNA surely encoding for subunit b of factor G.

The recombinant DNA vector containing cDNA encoding for the polypeptide obtained by Example 2 was transfected into reproducible host microorganisms, suitable animal cells, insect or cells thereof. They were screened using a marker of vector and (1→3)-β-D-glucan binding ability as indicators. The polypeptide of the present invention can be obtained by culturing or breeding of microorganisms, animal cells, insect or cells thereof having the recombinant DNA vector.

Industrial Applicability

In the present invention, subunit a of factor G of amebocyte lysate of horseshoe crab was isolated and purified, and the amino acid sequence and cDNA nucleotide sequence encoding for said amino acid sequence were determined.

The resultant sequence included a sequence of (1→3)-β-D-glucan binding region, and polypeptide corresponding to the binding region can be obtained by gene technological methods using the cDNA. The obtained polypeptide exhibits the following various effects.

(1) Recent increase of immunodisorder patients and aged populations markedly increased patients with opportunistic infections with secondary pathogens such as Candida and Aspergillus which generally have weak pathogenicity. However, their clinical diagnosis, particularly deep-seated mycoses of organs, was difficult without invasive procedure except special patterns of diseases and often definitely diagnosed by post-autopsy (Encyclopedia of Microbiology, Gihodo Shuppan Co., Ltd., 1989).

The diagnosis of deep-seated mycoses can be carried out by measuring (1→3)-β-D-glucan with ligand-receptor assay method using labeled polypeptide contained the (1→3)-β-D-glucan binding region or (1→3)-β-D-glucan labeled with radioactive isotopes, enzymes, fluorescent or luminous compounds. Said polypeptide may be immobilized on a solid phase such as microplate, test tube or beads for the specific detection of (→3)-β-D-glucan. These measuring methods specifically measure (1→3)-β-D-glucan derived from fungi in the body fluid for simple and rapid diagnosis of deep-seated mycoses.

(2) Medicines composed of an antifungal agent—conjugated polypeptide having a binding region with (1→3)-β-D-glucan exhibit potent affinity with lesions, and it will be new selective antifungal agents which specifically kill fungi which have (1→3)-β-D-glucan on their-cell walls exist in lesion.

(3) Furthermore, recent advances of gene manipulation technology often use yeasts as hosts of vector containing gene encoding for the aimed protein in its expression. This is because the production of glycoprotein is possible and mass culture is possible as well as bacteria. However, very small amount of residues of yeast having as a component often accompanies in the products, and its measurement and removal are required. An affinity chromatography with an affinity carrier of polypeptide contained (1→3)-β-D-glucan binding region bound to support may specifically remove or determine the residue of yeasts. In addition, confirmation of the absence of yeast cell component in the product after removal was performed by the measurement using polypeptide contained (1→3)-β-D-glucan binding site as described in (1) and provided more simple and specific confirmation than that of limulus amebocyte lysate.

What is claimed is:

1. An isolated nucleic acid fragment having a nucleotide sequence encoding a polypeptide having an amino acid sequence defined by amino acid residue numbers 247–387 in SEQ ID NO: 2.

2. An isolated nucleic acid fragment having a nucleotide sequence encoding the polypeptide having an amino acid sequence defined by amino acid residue numbers 4–236 in SEQ ID NO: 2.

3. An isolated nucleic acid fragment having a nucleotide sequence encoding a polypeptide having an amino acid sequence defined by amino acid residue numbers 391–654 in SEQ ID NO: 2.

4. An isolated nucleic acid fragment having a nucleotide sequence encoding SEQ ID NO: 2.

* * * * *

SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
      (A) LENGTH: 2409 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 114..2075

(xi) SEQUENCE DESCRIPTION: SEQ ID NO:1:

```
GTGGGGGGTT TAGTTGAAAC AGTAAATACG TTAACTGTTT AATCTTGTTA ATTGCAATGT     60

TGGTGTTGCT GTGTTGTGTT GTTTTGCATG TTGGTGTTGC AAGAATTTGC TGT AGC       116
                                                       Ser
                                                         1

CAC GAA CCA AAG TGG CAG CTC GTC TGG TCG GAT GAA TTT ACC AAT GGA     164
His Glu Pro Lys Trp Gln Leu Val Trp Ser Asp Glu Phe Thr Asn Gly
          5                  10                  15

ATA AGT TCT GAT TGG GAA TTT GAA ATG GGC AAT GGC CTC AAT GGT TGG     212
Ile Ser Ser Asp Trp Glu Phe Glu Met Gly Asn Gly Leu Asn Gly Trp
         20                  25                  30

GGT AAT AAC GAA CTG CAA TAT TAT CGT CGT GAA AAT GCC CAA GTT GAG     260
Gly Asn Asn Glu Leu Gln Tyr Tyr Arg Arg Glu Asn Ala Gln Val Glu
     35                  40                  45

GGA GGG AAA CTG GTA ATT ACT GCT AAA AGA GAA GAC TAT GAT GGC TTC     308
Gly Gly Lys Leu Val Ile Thr Ala Lys Arg Glu Asp Tyr Asp Gly Phe
 50                  55                  60                  65

AAA TAC ACT TCT GCT AGG CTG AAA ACC CAG TTT GAT AAA TCT TGG AAG     356
Lys Tyr Thr Ser Ala Arg Leu Lys Thr Gln Phe Asp Lys Ser Trp Lys
                 70                  75                  80

TAT GGT AAA ATT GAA GCC AAA ATG GCG ATT CCA TCA TTT CGG GGA GTC     404
Tyr Gly Lys Ile Glu Ala Lys Met Ala Ile Pro Ser Phe Arg Gly Val
             85                  90                  95

TGG GTG ATG TTC TGG ATG TCA GGA GAC AAC ACT AAT TAT GTT AGA TGG     452
Trp Val Met Phe Trp Met Ser Gly Asp Asn Thr Asn Tyr Val Arg Trp
            100                 105                 110

CCA TCT TCT GGT GAA ATT GAC TTT ATT GAA CAT AGA AAC ACT AAC AAT     500
Pro Ser Ser Gly Glu Ile Asp Phe Ile Glu His Arg Asn Thr Asn Asn
        115                 120                 125

GAA AAA GTC AGA GGA ACT ATT CAC TGG TCC ACT CCT GAC GGT GCT CAT     548
Glu Lys Val Arg Gly Thr Ile His Trp Ser Thr Pro Asp Gly Ala His
130                 135                 140                 145

GCG CAT CAT AAC AGA GAA AGT AAT ACA AAT GGG ATT GAT TAT CAC ATT     596
Ala His His Asn Arg Glu Ser Asn Thr Asn Gly Ile Asp Tyr His Ile
                150                 155                 160

TAT TCT GTA GAG TGG AAT TCT TCC ATT GTT AAA TGG TTT GTT AAT GGA     644
Tyr Ser Val Glu Trp Asn Ser Ser Ile Val Lys Trp Phe Val Asn Gly
            165                 170                 175

AAT CAA TAC TTT GAA GTG AAA ATT CAG GGA GGA GTA AAT GGG AAA AGT     692
Asn Gln Tyr Phe Glu Val Lys Ile Gln Gly Gly Val Asn Gly Lys Ser
        180                 185                 190

GCA TTT CGT AAC AAA GTT TTC GTT ATT TTA AAC ATG GCG ATT GGT GGA     740
Ala Phe Arg Asn Lys Val Phe Val Ile Leu Asn Met Ala Ile Gly Gly
```

-continued

```
              Ala Phe Arg Asn Lys Val Phe Val Ile Leu Asn Met Ala Ile Gly Gly
              195                 200                 205

AAC TGG CCA GGA TTC GAT GTT GCT GAC GAG GCT TTC CCT GCT AAA ATG        788
Asn Trp Pro Gly Phe Asp Val Ala Asp Glu Ala Phe Pro Ala Lys Met
210                 215                 220                 225

TAC ATT GAT TAT GTC CGT GTA TAC CAG GAT GCC AGT ACA TCT TCT CCT        836
Tyr Ile Asp Tyr Val Arg Val Tyr Gln Asp Ala Ser Thr Ser Ser Pro
                230                 235                 240

GTT GGG GAT ACC TCT TTA GAT GGT TAC TAT TTT GTC CAA AAC AGG CAC        884
Val Gly Asp Thr Ser Leu Asp Gly Tyr Tyr Phe Val Gln Asn Arg His
                245                 250                 255

AGT GAA TTG TAT CTT GAT GTC ACT GAT GCC AGT AAC GAA GAT GGA GCA        932
Ser Glu Leu Tyr Leu Asp Val Thr Asp Ala Ser Asn Glu Asp Gly Ala
            260                 265                 270

TTT CTG CAA CAA TGG TCT TAT AGT GGT AAT GAG AAC CAA CAG TTT GAT        980
Phe Leu Gln Gln Trp Ser Tyr Ser Gly Asn Glu Asn Gln Gln Phe Asp
275                 280                 285

TTT GAG CAT CTC GAA AAT AAT GTT TAT AAA ATT ACT AAT AAA AAA AGT       1028
Phe Glu His Leu Glu Asn Asn Val Tyr Lys Ile Thr Asn Lys Lys Ser
290                 295                 300                 305

GGA AAA TCT TTG GAT GTT TAT AAT TTT GGG ACT GAG AAT GGT GTT AGA       1076
Gly Lys Ser Leu Asp Val Tyr Asn Phe Gly Thr Glu Asn Gly Val Arg
                310                 315                 320

ATC CAA CAG TGG TCA TAT GGA GGG GCT CGC AAT CAG CAG TTT ACT GTA       1124
Ile Gln Gln Trp Ser Tyr Gly Gly Ala Arg Asn Gln Gln Phe Thr Val
                325                 330                 335

CAA AGT GTT GGT GAT GGT TAT TAT AAG ATT ATT CCA CGC GGC AGT GGA       1172
Gln Ser Val Gly Asp Gly Tyr Tyr Lys Ile Ile Pro Arg Gly Ser Gly
                340                 345                 350

AAG TTA GTG GAA GTA GCA GAT TTT AGT AAA GAT GCA GGA GGG AAG ATA       1220
Lys Leu Val Glu Val Ala Asp Phe Ser Lys Asp Ala Gly Gly Lys Ile
            355                 360                 365

CAA CAA TGG TCT GAT AAC AAC CAA TTA TCT GGA CAG TGG AAA CTT ATT       1268
Gln Gln Trp Ser Asp Asn Asn Gln Leu Ser Gly Gln Trp Lys Leu Ile
370                 375                 380                 385

AAA AGT AAA AGT TAT TCT AAA TTA ATT CAG GCA GAA AGT TAT TTT GAT       1316
Lys Ser Lys Ser Tyr Ser Lys Leu Ile Gln Ala Glu Ser Tyr Phe Asp
                390                 395                 400

TCC TCA AAA GTA CAA TTG GAA GAT ACC TCA GAT GTA GGA GGT GGG AAG       1364
Ser Ser Lys Val Gln Leu Glu Asp Thr Ser Asp Val Gly Gly Gly Lys
                405                 410                 415

AAT GTT AAA TGT GAT AAT GAA GGA GCC TGG ATG GCT TAT AAG GAT ATT       1412
Asn Val Lys Cys Asp Asn Glu Gly Ala Trp Met Ala Tyr Lys Asp Ile
            420                 425                 430

GAT TTC CCC AGT TCA GGT AAT TAT CGA ATA GAA TAC AGA GTA GCA AGT       1460
Asp Phe Pro Ser Ser Gly Asn Tyr Arg Ile Glu Tyr Arg Val Ala Ser
435                 440                 445

GAA CGT GCA GGA GGA AAG CTG TCT CTG GAT TTG AAT GCA GGC TCT ATA       1508
Glu Arg Ala Gly Gly Lys Leu Ser Leu Asp Leu Asn Ala Gly Ser Ile
450                 455                 460                 465

GTT CTT GGC ATG CTG GAT GTT CCT TCA ACA GGA GGA TGG CAG AAG TGG       1556
Val Leu Gly Met Leu Asp Val Pro Ser Thr Gly Gly Trp Gln Lys Trp
                470                 475                 480

ACC ACC ATT TCC CAT ACA GTG AAT GTG GAT TCA GGT ACA TAT AAC TTG       1604
Thr Thr Ile Ser His Thr Val Asn Val Asp Ser Gly Thr Tyr Asn Leu
                485                 490                 495

GGG ATC TAT GTT CAA CGA GCC AGC TGG AAT ATC AAC TGG ATA AAG ATT       1652
Gly Ile Tyr Val Gln Arg Ala Ser Trp Asn Ile Asn Trp Ile Lys Ile
                500                 505                 510
```

```
ACA AAA ATA CCT GAA CAG TCA AAT TTG AAT CAA GGG CGT CGT AAT TCT        1700
Thr Lys Ile Pro Glu Gln Ser Asn Leu Asn Gln Gly Arg Arg Asn Ser
    515                 520                 525

AAA TTA ATT CAG GCA GAA AGT TAT TTT AGT TAC TCA GAA GTA CAA CTG        1748
Lys Leu Ile Gln Ala Glu Ser Tyr Phe Ser Tyr Ser Glu Val Gln Leu
530                 535                 540                 545

GAA GAT ACC TTA GAT GTA GGA GGT GGA AAG AAT GTT AAA TGT GAT AAA        1796
Glu Asp Thr Leu Asp Val Gly Gly Gly Lys Asn Val Lys Cys Asp Lys
                550                 555                 560

GAA GGG GCC TGG ATG GCT TAC AAG GAT ATT GAT TTC CCC AGT TCA GGA        1844
Glu Gly Ala Trp Met Ala Tyr Lys Asp Ile Asp Phe Pro Ser Ser Gly
            565                 570                 575

AGT TAT CGA GTA GAA TAC AGA GTG GCA AGT GAA CGT GCA GGA GGA AAG        1892
Ser Tyr Arg Val Glu Tyr Arg Val Ala Ser Glu Arg Ala Gly Gly Lys
        580                 585                 590

CTG TCC CTA GAT TTG AAT GCA GGC TCT ATA GTG CTT GGC ATG CTG GAT        1940
Leu Ser Leu Asp Leu Asn Ala Gly Ser Ile Val Leu Gly Met Leu Asp
    595                 600                 605

ATT CCT TCA ACA GGA GGA TTG CAG AAG TGG ACC ACC ATT TCT CAT ATA        1988
Ile Pro Ser Thr Gly Gly Leu Gln Lys Trp Thr Thr Ile Ser His Ile
610                 615                 620                 625

GTG AAT GTG GAT TTA GGT ACA TAT AAC TTG GGA ATT TAT GTT CAA AAA        2036
Val Asn Val Asp Leu Gly Thr Tyr Asn Leu Gly Ile Tyr Val Gln Lys
                630                 635                 640

GCC AGT TGG AAT ATC AAT TGG ATT AGA ATT ACA AAA GTG TAGGATACAA         2085
Ala Ser Trp Asn Ile Asn Trp Ile Arg Ile Thr Lys Val
            645                 650

GAGCAAACCA ATTGTATTAT TTTGAAGAAA CAACAGCTGT TGACCATAAT CTTTGTTCAT      2145

TGAGAATTTA TCCAACTGTT ATAGAATCTA TCACCTTTCC AGATGTAACG CATTGCTGAT      2205

GGTTTTGAAC TAATAAATGA GGAGATTATA AGTGCTAATG TGTTTGTTAT ATCTTTAATT      2265

TTTAAAAACA AATTATCAAC TAACTTTTCA ATTCAGGCAT GGTGTTTCTC TTTTTAATCT      2325

GTATTTCTAA TAAATTAATG TCTTTAAGAG TTGTTTTGTT TACAATAAAT AAAGTTTGAT      2385

TGTGTGGGAT AAAAAAAAAA AAAA                                             2409

(2) INFORMATION FOR SEQ ID NO:2:

(i) SEQUENCE CHARACTERISTICS:
        (A) LENGTH: 654 amino acids
        (B) TYPE: amino acid
        (D) TOPOLOGY: linear (ii) MOLECULE TYPE: protein (xi) SEQUENCE DESCRIPTION: SEQ ID NO:2:

Ser His Glu Pro Lys Trp Gln Leu Val Trp Ser Asp Glu Phe Thr Asn
1               5                   10                  15

Gly Ile Ser Ser Asp Trp Glu Phe Glu Met Gly Asn Gly Leu Asn Gly
            20                  25                  30

Trp Gly Asn Asn Glu Leu Gln Tyr Tyr Arg Arg Glu Asn Ala Gln Val
        35                  40                  45

Glu Gly Gly Lys Leu Val Ile Thr Ala Lys Arg Glu Asp Tyr Asp Gly
    50                  55                  60

Phe Lys Tyr Thr Ser Ala Arg Leu Lys Thr Gln Phe Asp Lys Ser Trp
65                  70                  75                  80

Lys Tyr Gly Lys Ile Glu Ala Lys Met Ala Ile Pro Ser Phe Arg Gly
                85                  90                  95

Val Trp Val Met Phe Trp Met Ser Gly Asp Asn Thr Asn Tyr Val Arg
```

-continued

```
                100                 105                 110
Trp Pro Ser Ser Gly Glu Ile Asp Phe Ile Glu His Arg Asn Thr Asn
            115                 120                 125
Asn Glu Lys Val Arg Gly Thr Ile His Trp Ser Thr Pro Asp Gly Ala
        130                 135                 140
His Ala His His Asn Arg Glu Ser Asn Thr Asn Gly Ile Asp Tyr His
145                 150                 155                 160
Ile Tyr Ser Val Glu Trp Asn Ser Ser Ile Val Lys Trp Phe Val Asn
                165                 170                 175
Gly Asn Gln Tyr Phe Glu Val Lys Ile Gln Gly Val Asn Gly Lys
            180                 185                 190
Ser Ala Phe Arg Asn Lys Val Phe Val Ile Leu Asn Met Ala Ile Gly
        195                 200                 205
Gly Asn Trp Pro Gly Phe Asp Val Ala Asp Glu Ala Phe Pro Ala Lys
        210                 215                 220
Met Tyr Ile Asp Tyr Val Arg Val Tyr Gln Asp Ala Ser Thr Ser Ser
225                 230                 235                 240
Pro Val Gly Asp Thr Ser Leu Asp Gly Tyr Tyr Phe Val Gln Asn Arg
                245                 250                 255
His Ser Glu Leu Tyr Leu Asp Val Thr Asp Ala Ser Asn Glu Asp Gly
            260                 265                 270
Ala Phe Leu Gln Gln Trp Ser Tyr Ser Gly Asn Glu Asn Gln Gln Phe
        275                 280                 285
Asp Phe Glu His Leu Glu Asn Asn Val Tyr Lys Ile Thr Asn Lys Lys
        290                 295                 300
Ser Gly Lys Ser Leu Asp Val Tyr Asn Phe Gly Thr Glu Asn Gly Val
305                 310                 315                 320
Arg Ile Gln Gln Trp Ser Tyr Gly Gly Ala Arg Asn Gln Gln Phe Thr
                325                 330                 335
Val Gln Ser Val Gly Asp Gly Tyr Tyr Lys Ile Ile Pro Arg Gly Ser
            340                 345                 350
Gly Lys Leu Val Glu Val Ala Asp Phe Ser Lys Asp Ala Gly Gly Lys
        355                 360                 365
Ile Gln Gln Trp Ser Asp Asn Asn Gln Leu Ser Gly Gln Trp Lys Leu
        370                 375                 380
Ile Lys Ser Lys Ser Tyr Ser Lys Leu Ile Gln Ala Glu Ser Tyr Phe
385                 390                 395                 400
Asp Ser Ser Lys Val Gln Leu Glu Asp Thr Ser Asp Val Gly Gly Gly
                405                 410                 415
Lys Asn Val Lys Cys Asp Asn Glu Gly Ala Trp Met Ala Tyr Lys Asp
            420                 425                 430
Ile Asp Phe Pro Ser Ser Gly Asn Tyr Arg Ile Glu Tyr Arg Val Ala
        435                 440                 445
Ser Glu Arg Ala Gly Gly Lys Leu Ser Leu Asp Leu Asn Ala Gly Ser
        450                 455                 460
Ile Val Leu Gly Met Leu Asp Val Pro Ser Thr Gly Gly Trp Gln Lys
465                 470                 475                 480
Trp Thr Thr Ile Ser His Thr Val Asn Val Asp Ser Gly Thr Tyr Asn
                485                 490                 495
Leu Gly Ile Tyr Val Gln Arg Ala Ser Trp Asn Ile Asn Trp Ile Lys
            500                 505                 510
Ile Thr Lys Ile Pro Glu Gln Ser Asn Leu Asn Gln Gly Arg Arg Asn
        515                 520                 525
```

```
Ser Lys Leu Ile Gln Ala Glu Ser Tyr Phe Ser Tyr Ser Glu Val Gln
    530                 535                 540

Leu Glu Asp Thr Leu Asp Val Gly Gly Lys Asn Val Lys Cys Asp
545                 550                 555                 560

Lys Glu Gly Ala Trp Met Ala Tyr Lys Asp Ile Asp Phe Pro Ser Ser
                    565                 570                 575

Gly Ser Tyr Arg Val Glu Tyr Arg Val Ala Ser Glu Arg Ala Gly Gly
                580                 585                 590

Lys Leu Ser Leu Asp Leu Asn Ala Gly Ser Ile Val Leu Gly Met Leu
            595                 600                 605

Asp Ile Pro Ser Thr Gly Gly Leu Gln Lys Trp Thr Thr Ile Ser His
    610                 615                 620

Ile Val Asn Val Asp Leu Gly Thr Tyr Asn Leu Gly Ile Tyr Val Gln
625                 630                 635                 640

Lys Ala Ser Trp Asn Ile Asn Trp Ile Arg Ile Thr Lys Val
                645                 650
```

(2) INFORMATION FOR SEQ ID NO:3:

(i) SEQUENCE CHARACTERISTICS:
        (A) LENGTH: 1979 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 194..1027

(xi) SEQUENCE DESCRIPTION: SEQ ID NO:3:

```
GAAGACAAGA GAGTTGAAAC AACCATAGCC TGTTTGCTTA TGACTTTCAA TAAGAGATAC        60

TCGGCTTAAA GGGAACTGAC TTATTCGTAG AGGCTATACC ATGGATATCA GTTTCCTGGT       120

TTTTATCACA CTGTCTATGG CTCTCTTCTC GAGCAACGTG ACAGGAACGT CAGTAACATC       180

AAGGGTACGA CGT GGA ATA AAT GAA AAA CAT TGT GGG TTC CGA CCA GTA          229
            Gly Ile Asn Glu Lys His Cys Gly Phe Arg Pro Val
              1               5                  10

ATT ACA AGA ATT ATT GGT GGA GGA ATA GCG ACG CCT CAT TCA TGG CCG         277
Ile Thr Arg Ile Ile Gly Gly Gly Ile Ala Thr Pro His Ser Trp Pro
        15                  20                  25

TGG ATG GTT GGA ATT TTC AAA GTA AAT CCT CAC CGT TTC CTT TGT GGT         325
Trp Met Val Gly Ile Phe Lys Val Asn Pro His Arg Phe Leu Cys Gly
    30                  35                  40

GGA TCT ATT ATT AAT AAA GTC TCT GTT GTT ACT GCC GCC CAT TGT CTT         373
Gly Ser Ile Ile Asn Lys Val Ser Val Val Thr Ala Ala His Cys Leu
45                  50                  55                  60

GTG ACG CAG TTT GGA AAC AGA CAG AAT TAT TCT ATC TTC GTA AGA GTT         421
Val Thr Gln Phe Gly Asn Arg Gln Asn Tyr Ser Ile Phe Val Arg Val
                65                  70                  75

GGA GCC CAT GAC ATA GAC AAT TCG GGT ACA AAT TAT CAA GTG GAT AAA         469
Gly Ala His Asp Ile Asp Asn Ser Gly Thr Asn Tyr Gln Val Asp Lys
            80                  85                  90

GTT ATT GTT CAC CAG GGC TAC AAA CAC CAT TCA CAC TAC TAC GAT ATC         517
Val Ile Val His Gln Gly Tyr Lys His His Ser His Tyr Tyr Asp Ile
        95                  100                 105

GGT TTG ATT TTA CTC TCG AAA CCA GTC GAA TAC AAC GAC AAA ATA CAG         565
Gly Leu Ile Leu Leu Ser Lys Pro Val Glu Tyr Asn Asp Lys Ile Gln
    110                 115                 120
```

```
CCT GTC TGT ATT CCT GAG TTC AAC AAA CCT CAC GTG AAC TTG AAC AAT      613
Pro Val Cys Ile Pro Glu Phe Asn Lys Pro His Val Asn Leu Asn Asn
125                 130                 135                 140

ATT AAG GTC GTC ATT ACT GGT TGG GGT GTT ACT GGG AAA GCT ACT GAG      661
Ile Lys Val Val Ile Thr Gly Trp Gly Val Thr Gly Lys Ala Thr Glu
                145                 150                 155

AAA CGT AAC GTT CTT CGT GAA TTG GAG TTG CCC GTG GTT ACA AAC GAA      709
Lys Arg Asn Val Leu Arg Glu Leu Glu Leu Pro Val Val Thr Asn Glu
            160                 165                 170

CAG TGC AAC AAA TCT TAT CAG ACA CTC CCA TTC TCA AAA TTG AAC CGA      757
Gln Cys Asn Lys Ser Tyr Gln Thr Leu Pro Phe Ser Lys Leu Asn Arg
        175                 180                 185

GGA ATC ACT AAC GAC ATG ATT TGT GCG GGG TTT CCG GAA GGA GGG AAA      805
Gly Ile Thr Asn Asp Met Ile Cys Ala Gly Phe Pro Glu Gly Gly Lys
    190                 195                 200

GAT GCT TGT CAG GGC GAC TCT GGT GGT CCC CTG ATG TAT CAG AAT CCA      853
Asp Ala Cys Gln Gly Asp Ser Gly Gly Pro Leu Met Tyr Gln Asn Pro
205                 210                 215                 220

ACA ACA GGA AGA GTG AAA ATA GTT GGA GTT GTA TCA TTT GGG TTC GAA      901
Thr Thr Gly Arg Val Lys Ile Val Gly Val Val Ser Phe Gly Phe Glu
                225                 230                 235

TGT GCT CGT CCC AAC TTC CCC GGT GTT TAC ACG CGC CTC TCG AGC TAC      949
Cys Ala Arg Pro Asn Phe Pro Gly Val Tyr Thr Arg Leu Ser Ser Tyr
            240                 245                 250

GTT AAC TGG CTC CAG GAA ATC ACC TTC GGA CAG TCA CTC GCT TCT TTA      997
Val Asn Trp Leu Gln Glu Ile Thr Phe Gly Gln Ser Leu Ala Ser Leu
        255                 260                 265

TTT GAA GTT GTA CCA ATA TTT ATA CCC GAG TGAGACTGAA GATAAATATT       1047
Phe Glu Val Val Pro Ile Phe Ile Pro Glu
    270                 275

GAAGAGAAAT CTAGAATAAT GTACAATATA AGAAGCCTGA AATTACTGAA ATAGAAAGGC   1107

GCGTGATGAG AAATACGTTT CAAATTTTAT TTTTTATTAA CTTTATTGTG TTTAACTATT   1167

CTTTACGTGG GACATGAAAT ATAAATCTTT ATTTCTTCTT TATATACTTT AGATTTTCAT   1227

TTCATCTATC TTTATCAGTT TTGTAATGTT ACTAATAATA TTTCTTATGG CACGGATCGA   1287

GCCTCGTGAA TCACAGTAAA TAATAATAAT TATAAAATCA CACATTATTA AAAGCAATAG   1347

CATTCAGAGT GAGTAACATA TAAACTTCAC TATGAGTGGA CTTTTTTATT CACATTTTAA   1407

GTTCATTACT AACTGTTGGG AGGTCTTTAT ATTGTTGTAT ATTTATATAT TAATTAGGTT   1467

GGTTTAGTAC ATTGTTGTTA ATGGTGGAAT AGGGCGTAGG TTTTAAATGT GTTTGCAAAA   1527

AAACAAACAA AACAAGTAAT GGTGGATGAT GGTTCCAAAG TAACCGAAAG AACACTTTGA   1587

ACATTTTTAT ACAAAAATTT ATGTTTTAAA ATACGAGTAT ATACAATCGA TCTCTAAGTA   1647

CAAGAAAAAC TGAAGTGTTC ATTCAGGTTT AACAGTGCAA CTTAAATCAA CAGTTAGTTG   1707

TTCACTAAAC ATTACAATTT GATCCTTTAT AAACGCTAAT ACTGTTTAAA CAGTCAGTAA   1767

TAATACAGTA TCATAGCATA TCATATATGA AGGTATTTTA ACATTCTATA TACAAAGCCA   1827

GAATTGAAAA CGGTAATATT TTGTACGATT AGTGAATTAT TGTTTTTAAG AACAAACTGG   1887

TATCAAATTT AAAATATGAA TCTGTGATTT AATATTTTTT ACAACGTTCT AACTTACCAC   1947

TTTTGTTGTG AATAAAGGTG TTTACAAATG GA                                1979
```

(2) INFORMATION FOR SEQ ID NO:4:

(i) SEQUENCE CHARACTERISTICS:
        (A) LENGTH: 278 amino acids
        (B) TYPE: amino acid (D) TOPOLOGY: linear (ii) MOLECULE TYPE: protein (xi) SEQUENCE DESCRIPTION: SEQ ID NO:4:

```
Gly Ile Asn Glu Lys His Cys Gly Phe Arg Pro Val Ile Thr Arg Ile
 1               5                  10                  15

Ile Gly Gly Gly Ile Ala Thr Pro His Ser Trp Pro Trp Met Val Gly
                20                  25                  30

Ile Phe Lys Val Asn Pro His Arg Phe Leu Cys Gly Gly Ser Ile Ile
                35                  40                  45

Asn Lys Val Ser Val Val Thr Ala Ala His Cys Leu Val Thr Gln Phe
50                      55                  60

Gly Asn Arg Gln Asn Tyr Ser Ile Phe Val Arg Val Gly Ala His Asp
65                  70                  75                  80

Ile Asp Asn Ser Gly Thr Asn Tyr Gln Val Asp Lys Val Ile Val His
                85                  90                  95

Gln Gly Tyr Lys His His Ser His Tyr Tyr Asp Ile Gly Leu Ile Leu
                100                 105                 110

Leu Ser Lys Pro Val Glu Tyr Asn Asp Lys Ile Gln Pro Val Cys Ile
        115                 120                 125

Pro Glu Phe Asn Lys Pro His Val Asn Leu Asn Asn Ile Lys Val Val
130                 135                 140

Ile Thr Gly Trp Gly Val Thr Gly Lys Ala Thr Glu Lys Arg Asn Val
145                 150                 155                 160

Leu Arg Glu Leu Glu Leu Pro Val Val Thr Asn Glu Gln Cys Asn Lys
                165                 170                 175

Ser Tyr Gln Thr Leu Pro Phe Ser Lys Leu Asn Arg Gly Ile Thr Asn
                180                 185                 190

Asp Met Ile Cys Ala Gly Phe Pro Glu Gly Gly Lys Asp Ala Cys Gln
            195                 200                 205

Gly Asp Ser Gly Gly Pro Leu Met Tyr Gln Asn Pro Thr Thr Gly Arg
210                 215                 220

Val Lys Ile Val Gly Val Val Ser Phe Gly Phe Glu Cys Ala Arg Pro
225                 230                 235                 240

Asn Phe Pro Gly Val Tyr Thr Arg Leu Ser Ser Tyr Val Asn Trp Leu
                245                 250                 255

Gln Glu Ile Thr Phe Gly Gln Ser Leu Ala Ser Leu Phe Glu Val Val
                260                 265                 270

Pro Ile Phe Ile Pro Glu
        275
```

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /note= "TABLE 1, PEPTIDE 1"

(xi) SEQUENCE DESCRIPTION: SEQ ID NO:5:

Ser Xaa Glu Pro Lys Xaa Gln Leu Val

```
1               5

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /note= "TABLE 1, PEPTIDE 2"

(xi) SEQUENCE DESCRIPTION: SEQ ID NO:6:

Arg Glu Asp Tyr Asp Gly Phe Lys
1               5

(2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /note= "TABLE 1, PEPTIDE 3"

(xi) SEQUENCE DESCRIPTION: SEQ ID NO:7:

Tyr Thr Ser Ala Arg Leu Lys
1               5

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "TABLE 1, PEPTIDE 4"

(xi) SEQUENCE DESCRIPTION: SEQ ID NO:8:

Thr Gln Phe Asp Lys
1               5

(2) INFORMATION FOR SEQ ID NO:9:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..26
```

(D) OTHER INFORMATION: /note= "TABLE 1, PEPTIDE 7"

(xi) SEQUENCE DESCRIPTION: SEQ ID NO:9:

Met Ala Ile Pro Ser Phe Arg Gly Val Trp Val Met Phe Trp Met Ser
1               5                   10                  15

Gly Xaa Asn Thr Asn Tyr Val Xaa Xaa Pro
            20                  25

(2) INFORMATION FOR SEQ ID NO:10:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Peptide
          (B) LOCATION: 1..6
          (D) OTHER INFORMATION: /note= "TABLE 1, PEPTIDE 8"

(xi) SEQUENCE DESCRIPTION: SEQ ID NO:10:

Ser Ala Phe Arg Asn Lys
1               5

(2) INFORMATION FOR SEQ ID NO:11:

(i) SEQUENCE CHARACTERISTICS:
          (A) LENGTH: 19 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Peptide
          (B) LOCATION: 1..19
          (D) OTHER INFORMATION: /note= "TABLE 1, PEPTIDE 9"

(xi) SEQUENCE DESCRIPTION: SEQ ID NO:11:

Val Phe Val Ile Leu Asn Met Ala Ile Gly Gly Asn Xaa Pro Gly Phe
1               5                   10                  15

Xaa Val Ala (2) INFORMATION FOR SEQ ID NO:12:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Peptide
          (B) LOCATION: 1..8
          (D) OTHER INFORMATION: /note= "TABLE 1, PEPTIDE 10"

(xi) SEQUENCE DESCRIPTION: SEQ ID NO:12:

Ile Ile Pro Arg Gly Ser Gly Lys
1               5

(2) INFORMATION FOR SEQ ID NO:13:

(i) SEQUENCE CHARACTERISTICS:

(A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..13
        (D) OTHER INFORMATION: /note= "TABLE 1, PEPTIDE 11"

(xi) SEQUENCE DESCRIPTION: SEQ ID NO:13:

Val Gln Leu Glu Asp Thr Ser Asp Val Gly Gly Gly Lys
1               5                  10

(2) INFORMATION FOR SEQ ID NO:14:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..11
        (D) OTHER INFORMATION: /note= "TABLE 1, PEPTIDE 12"

(xi) SEQUENCE DESCRIPTION: SEQ ID NO:14:

Cys Asp Asn Glu Gly Ala Trp Met Ala Tyr Lys
1               5                  10

(2) INFORMATION FOR SEQ ID NO:15:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..17
        (D) OTHER INFORMATION: /note= "TABLE 1, PEPTIDE 13"

(xi) SEQUENCE DESCRIPTION: SEQ ID NO:15:

Asp Ile Asp Phe Pro Ser Ser Gly Asn Tyr Xaa Ile Glu Tyr Xaa Val
1               5                  10                  15

Ala (2) INFORMATION FOR SEQ ID NO:16:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..16
        (D) OTHER INFORMATION: /note= "TABLE 1, PEPTIDE 14"

(xi) SEQUENCE DESCRIPTION: SEQ ID NO:16:

```
Leu Ile Gln Ala Glu Xaa Tyr Phe Xaa Tyr Xaa Glu Val Gln Leu Glu
1               5                  10                  15
```

(2) INFORMATION FOR SEQ ID NO:17:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /note= "TABLE 1, PEPTIDE 15"

(xi) SEQUENCE DESCRIPTION: SEQ ID NO:17:

```
Glu Gly Ala Trp Met Ala Tyr Lys
1               5
```

(2) INFORMATION FOR SEQ ID NO:18:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..19
        (D) OTHER INFORMATION: /note= "TABLE 1, PEPTIDE 16"

(xi) SEQUENCE DESCRIPTION: SEQ ID NO:18:

```
Val Arg Gly Thr Ile His Trp Ser Thr Pro Asp Gly Ala His Ala His
1               5                  10                  15
His Asn Arg
```

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..25
        (D) OTHER INFORMATION: /product= "DNA SEQUENCE A'"

(xi) SEQUENCE DESCRIPTION: SEQ ID NO:19:

```
CGGAGCTCGA RGAYTAYGAY GGNTT                                    25
```

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (ix) FEATURE:

(A) NAME/KEY: misc_feature
        (B) LOCATION: 1..26
        (D) OTHER INFORMATION: /product= "DNA SEQUENCE B'"

(xi) SEQUENCE DESCRIPTION: SEQ ID NO:20:

CGGAATTCCA TCCARAACAT NACCCA                                               26

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..20
        (D) OTHER INFORMATION: /product= "DNA SEQUENCE SECTION 8
              OF SPECIFICATION"

(xi) SEQUENCE DESCRIPTION: SEQ ID NO:21:

AGCCACGAAC CAAAGTGGCA                                                      20

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..24
        (D) OTHER INFORMATION: /product= "DNA PROBE SECTION 8 OF
              SPECIFICATION"

(xi) SEQUENCE DESCRIPTION: SEQ ID NO:22:

AAACAGACCA TGAGCCACGA ACCA                                                 24

(2) INFORMATION FOR SEQ ID NO:23:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "TABLE 2, PEPTIDE 1"

(xi) SEQUENCE DESCRIPTION: SEQ ID NO:23:

Gly Ile Asn Glu Lys
1               5

(2) INFORMATION FOR SEQ ID NO:24:

(i) SEQUENCE CHARACTERISTICS:
        (A) LENGTH: 9 amino acids
        (B) TYPE: amino acid
        (C) STRANDEDNESS: single
        (D) TOPOLOGY: linear

```
        (ii) MOLECULE TYPE: peptide (ix) FEATURE:
              (A) NAME/KEY: Peptide
              (B) LOCATION: 1..9
              (D) OTHER INFORMATION: /note= "TABLE 2, PEPTIDE 2"

(xi) SEQUENCE DESCRIPTION: SEQ ID NO:24:

Xaa Xaa Gly Phe Xaa Pro Val Ile Thr
1               5

(2) INFORMATION FOR SEQ ID NO:25:

(i) SEQUENCE CHARACTERISTICS:
              (A) LENGTH: 19 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1..19
              (D) OTHER INFORMATION: /note= "TABLE 2, PEPTIDE 3"

(xi) SEQUENCE DESCRIPTION: SEQ ID NO:25:

Ile Ile Gly Gly Gly Ile Ala Thr Pro His Ser Xaa Pro Xaa Met Val
1               5                   10                  15

Gly Ile Phe (2) INFORMATION FOR SEQ ID NO:26:

(i) SEQUENCE CHARACTERISTICS:
              (A) LENGTH: 37 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1..37
              (D) OTHER INFORMATION: /note= "TABLE 2, PEPTIDE 5"

(xi) SEQUENCE DESCRIPTION: SEQ ID NO:26:

Val Xaa Val Val Thr Ala Ala His Cys Leu Val Thr Gln Phe Gly Asn
1               5                   10                  15

Arg Gln Xaa Tyr Ser Ile Phe Val Arg Val Gly Ala His Xaa Ile Xaa
                20                  25                  30

Asn Ser Gly Thr Asn
            35

(2) INFORMATION FOR SEQ ID NO:27:

(i) SEQUENCE CHARACTERISTICS:
              (A) LENGTH: 11 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1..11
              (D) OTHER INFORMATION: /note= "TABLE 2, PEPTIDE 6"
```

(xi) SEQUENCE DESCRIPTION: SEQ ID NO:27:

Val Val Ile Thr Gly Trp Gly Val Thr Gly Lys
1               5                  10

(2) INFORMATION FOR SEQ ID NO:28:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..18
            (D) OTHER INFORMATION: /note= "TABLE 2, PEPTIDE 7"

(xi) SEQUENCE DESCRIPTION: SEQ ID NO:28:

Asn Val Leu Arg Glu Leu Glu Leu Pro Val Val Thr Asn Glu Gln Cys
1               5                  10                  15

Xaa Lys (2) INFORMATION FOR SEQ ID NO:29:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..9
            (D) OTHER INFORMATION: /note= "TABLE 2, PEPTIDE 8"

(xi) SEQUENCE DESCRIPTION: SEQ ID NO:29:

Ser Tyr Gln Thr Leu Pro Phe Ser Lys
1               5

(2) INFORMATION FOR SEQ ID NO:30:

(i) SEQUENCE CHARACTERISTICS:
            (A) LENGTH: 19 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..19
            (D) OTHER INFORMATION: /note= "TABLE 1, PEPTIDE 9"

(xi) SEQUENCE DESCRIPTION: SEQ ID NO:30:

Leu Asn Arg Gly Ile Thr Asn Asp Met Ile Cys Ala Gly Phe Pro Glu
1               5                  10                  15

Gly Gly Lys (2) INFORMATION FOR SEQ ID NO:31:

(i) SEQUENCE CHARACTERISTICS:
            (A) LENGTH: 22 amino acids
            (B) TYPE: amino acid
            (C) STRANDEDNESS: single (D) TOPOLOGY: linear (ii) MOLECULE TYPE: peptide (ix) FEATURE:
            (A) NAME/KEY: Peptide
            (B) LOCATION: 1..22
            (D) OTHER INFORMATION: /note= "TABLE 2, PEPTIDE 10"

(xi) SEQUENCE DESCRIPTION: SEQ ID NO:31:

Asp Ala Cys Gln Gly Asp Ser Gly Gly Pro Leu Met Tyr Gln Asn Pro
1               5                  10                  15

Thr Thr Gly Arg Val Lys
            20

(2) INFORMATION FOR SEQ ID NO:32:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 1..25
            (D) OTHER INFORMATION: /product= "DNA SEQUENCE C'"

(xi) SEQUENCE DESCRIPTION: SEQ ID NO:32:

CGGAGCTCAA YGARCARTGY AAYAA                                      25

(2) INFORMATION FOR SEQ ID NO:33:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 1..25
            (D) OTHER INFORMATION: /product= "DNA SEQUENCE D'"

(xi) SEQUENCE DESCRIPTION: SEQ ID NO:33:

CGGAATTCGT NGGRTTYTGR TACAT                                      25

(2) INFORMATION FOR SEQ ID NO:34:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..4
            (D) OTHER INFORMATION: /note= "PEPTIDE MOTIF"

(xi) SEQUENCE DESCRIPTION: SEQ ID NO:34:

Gln Gln Trp Ser
1

-continued (2) INFORMATION FOR SEQ ID NO:35:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "A CHAIN PEPTIDE SEQUENCE
            FROM FIG. 1"

(xi) SEQUENCE DESCRIPTION: SEQ ID NO:35:

Val Leu Gly Arg Thr
1           5

(2) INFORMATION FOR SEQ ID NO:36:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "SECTION OF PEPTIDE C
            SEQUENCE SET FORTH IN FIG.1"

(xi) SEQUENCE DESCRIPTION: SEQ ID NO:36:

Val Ser Gly Arg Gly
1           5

(2) INFORMATION FOR SEQ ID NO:37:

(i) SEQUENCE CHARACTERISTICS:
        (A) LENGTH: 262 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Protein
        (B) LOCATION: 1..262
        (D) OTHER INFORMATION: /note= "BG1 A1 SEQUENCE (FIGURE 2)"

(xi) SEQUENCE DESCRIPTION: SEQ ID NO:37:

Ala Gly Met Asn Leu Ile Trp Gln Asp Glu Phe Asn Gly Thr Thr Leu
1           5                 10                 15

Asp Thr Ser Lys Trp Asn Tyr Glu Thr Gly Tyr Tyr Leu Asn Asn Asp
              20                   25                 30

Pro Ala Thr Trp Gly Trp Gly Asn Ala Glu Leu Gln His Tyr Thr Asn
              35                   40                 45

Ser Thr Gln Asn Val Tyr Val Gln Asp Gly Lys Leu Asn Ile Lys Ala
            50                   55                 60

Met Asn Asp Ser Lys Ser Phe Pro Gln Asp Pro Asn Arg Tyr Ala Gln
65                 70                 75                 80

Tyr Ser Ser Gly Lys Ile Asn Thr Lys Asp Lys Leu Ser Leu Lys Tyr
              85                   90                 95

```
Gly Arg Val Asp Phe Arg Ala Lys Leu Pro Thr Gly Asp Gly Val Trp
            100                 105                 110
Pro Ala Leu Trp Met Leu Pro Lys Asp Ser Val Tyr Gly Thr Trp Ala
            115                 120                 125
Ala Ser Gly Glu Ile Asp Val Met Glu Ala Arg Gly Arg Leu Pro Gly
130                 135                 140
Ser Val Ser Gly Thr Ile His Phe Gly Gly Gln Trp Pro Val Asn Gln
145                 150                 155                 160
Ser Ser Gly Gly Asp Tyr His Phe Pro Glu Gly Gln Thr Phe Ala Asn
                165                 170                 175
Asp Tyr His Val Tyr Ser Val Val Trp Glu Glu Asp Asn Ile Lys Trp
                180                 185                 190
Tyr Val Asp Gly Lys Phe Phe Tyr Lys Val Thr Asn Gln Gln Trp Tyr
            195                 200                 205
Ser Thr Ala Ala Pro Asn Asn Pro Asn Ala Pro Phe Asp Glu Pro Phe
            210                 215                 220
Tyr Leu Ile Met Asn Leu Ala Val Gly Gly Asn Phe Asp Gly Gly Arg
225                 230                 235                 240
Thr Pro Asn Ala Ser Asp Ile Pro Ala Thr Met Gln Val Asp Tyr Val
                245                 250                 255
Arg Val Tyr Lys Glu Gln
            260
```

(2) INFORMATION FOR SEQ ID NO:38:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..137
        (D) OTHER INFORMATION: /note= "XYN Z SEQUENCE (FIGURE 3)"

(xi) SEQUENCE DESCRIPTION: SEQ ID NO:38:

```
Asn Thr Arg Ile Glu Ala Glu Asp Tyr Asp Gly Ile Asn Ser Ser Ser
1               5                   10                  15
Ile Glu Ile Ile Gly Val Pro Pro Glu Gly Arg Gly Ile Gly Tyr
            20                  25                  30
Ile Thr Ser Gly Asp Tyr Leu Val Tyr Lys Ser Ile Asp Phe Gly Asn
            35                  40                  45
Gly Ala Thr Ser Phe Lys Ala Lys Val Ala Asn Ala Asn Thr Ser Asn
50                  55                  60
Ile Glu Leu Arg Leu Asn Gly Pro Asn Gly Thr Leu Ile Gly Thr Leu
65                  70                  75                  80
Ser Val Lys Ser Thr Gly Asp Trp Asn Thr Tyr Glu Glu Gln Thr Cys
                85                  90                  95
Ser Ile Ser Lys Val Thr Gly Ile Asn Asp Leu Tyr Leu Val Phe Lys
            100                 105                 110
Gly Pro Val Asn Ile Asp Trp Phe Thr Phe Gly Val Glu Ser Ser Ser
            115                 120                 125
Thr Gly Leu Gly Asp Leu Asn Gly Asp
    130                 135
```

(2) INFORMATION FOR SEQ ID NO:39:

(i) SEQUENCE CHARACTERISTICS:
        (A) LENGTH: 127 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..127
        (D) OTHER INFORMATION: /note= "XLN A SEQUENCE (FIGURE 4)"

(xi) SEQUENCE DESCRIPTION: SEQ ID NO:39:

```
Ala Asp Gly Gly Gln Ile Lys Gly Val Gly Ser Gly Arg Cys Leu Asp
  1               5                  10                  15

Val Pro Asp Ala Ser Thr Ser Asp Gly Thr Gln Leu Gln Leu Trp Asp
                 20                  25                  30

Cys His Ser Gly Thr Asn Gln Gln Trp Ala Ala Thr Asp Ala Gly Glu
             35                  40                  45

Leu Arg Val Tyr Gly Asp Lys Cys Leu Asp Ala Ala Gly Thr Ser Asn
         50                  55                  60

Gly Ser Lys Val Gln Ile Tyr Ser Cys Trp Gly Gly Asp Asn Gln Lys
 65                  70                  75                  80

Trp Arg Leu Asn Ser Asp Gly Ser Val Val Gly Val Gln Ser Gly Leu
                 85                  90                  95

Cys Leu Asp Ala Val Gly Asn Gly Thr Ala Asn Gly Thr Leu Ile Gln
                100                 105                 110

Leu Tyr Thr Cys Ser Asn Gly Ser Asn Gln Arg Trp Thr Arg Thr
                115                 120                 125
```